United States Patent
Nord et al.

(10) Patent No.: US 9,387,345 B2
(45) Date of Patent: Jul. 12, 2016

(54) APPARATUS AND METHOD PERTAINING TO DETERMINING A SPATIALLY-VARIANT NORMAL TISSUE CONSTRAINT AS A FUNCTION OF DOSE DISTRIBUTION

(75) Inventors: Janne Nord, Espoo (FI); Jarkko Peltola, Tuusula (FI)

(73) Assignee: Varian Medical Systems International AG, Cham (CH)

( * ) Notice: Subject to any disclaimer, the term of this patent is extended or adjusted under 35 U.S.C. 154(b) by 825 days.

(21) Appl. No.: 13/548,590

(22) Filed: Jul. 13, 2012

(65) Prior Publication Data

US 2014/0018602 A1 Jan. 16, 2014

(51) Int. Cl.
*A61N 5/10* (2006.01)

(52) U.S. Cl.
CPC ....... *A61N 5/1031* (2013.01); *A61N 2005/1041* (2013.01)

(58) Field of Classification Search
USPC ...................................... 378/65, 64
See application file for complete search history.

(56) References Cited

U.S. PATENT DOCUMENTS

| | | |
|---|---|---|
| 2008/0008291 A1 | 1/2008 | Alakuijala et al. |
| 2008/0226030 A1* | 9/2008 | Otto ................................. 378/65 |
| 2010/0104068 A1* | 4/2010 | Kilby et al. ..................... 378/65 |
| 2011/0069815 A1 | 3/2011 | Nord et al. |
| 2012/0197058 A1* | 8/2012 | Shukla et al. .................... 600/1 |

FOREIGN PATENT DOCUMENTS

| | | |
|---|---|---|
| WO | 2007/002642 A2 | 1/2007 |
| WO | 2008/035213 A2 | 3/2008 |

OTHER PUBLICATIONS

Beck, Ewa; Authorized Officer; PCT Search Report and Written Opinion from related PCT/EP2013/064903 dated Oct. 15, 2013; 9 pages.

* cited by examiner

*Primary Examiner* — Kiet T Nguyen
(74) *Attorney, Agent, or Firm* — Fitch, Even, Tabin & Flannery LLP

(57) ABSTRACT

A control circuit optimizes a radiation-treatment plan (as regards treating at least one target volume for a given patient) by automatically determining a spatially-variant normal tissue constraint as a function, at least in part, of dose distribution for normal tissue that is proximal to the target volume. If desired, the control circuit can repeatedly determine spatially-variant normal tissue constraints while optimizing the radiation-treatment plan. This automatic determination can comprise evaluating dose distributions at specific different distances from the target volume. So configured, the control circuit can effect such evaluation by penalizing, during the optimization of the radiation-treatment plan, dose distribution levels that exceed a predetermined distribution property (such as an aggregation value for the dose values including, but not limited to, an average value of dose values for each of the given specific different distances) at a given one of the specific different distances.

18 Claims, 1 Drawing Sheet

APPARATUS AND METHOD PERTAINING TO DETERMINING A SPATIALLY-VARIANT NORMAL TISSUE CONSTRAINT AS A FUNCTION OF DOSE DISTRIBUTION

TECHNICAL FIELD

This invention relates generally to the optimization of radiation-treatment plans.

BACKGROUND

The use of radiation to treat medical conditions comprises a known area of prior art endeavor. For example, radiation therapy comprises an important component of many treatment plans for reducing or eliminating unwanted tumors. Unfortunately, applied radiation does not inherently discriminate between unwanted materials and adjacent healthy tissues, organs, or the like that are desired or even critical to continued survival of the patient. As a result, radiation is ordinarily applied in a carefully administered manner to at least attempt to restrict the radiation to a given target volume.

Treatment plans typically serve to specify any number of operating parameters as pertain to the administration of such treatment with respect to a given patient. For example, many treatment plans provide for exposing the target volume to possibly varying dosages of radiation from a number of different directions using variable beam shapes. Arc therapy, for example, comprises one such approach.

Such treatment plans are often optimized prior to use. (As used herein, "optimization" will be understood to refer to improving upon a candidate treatment plan without necessarily ensuring that the optimized result is, in fact, the singular best solution.) Many optimization approaches use an automated incremental methodology where various optimization results are calculated and tested in turn using a variety of automatically-modified (i.e., "incremented") treatment plan optimization parameters.

Many treatment plans provide for delivering radiation towards a target tissue from a plurality of different angles. Such an approach may create so-called hotspots (i.e., local volumes of higher radiation doses) in healthy tissue. By one approach hotspots are attempted to be minimized or reduced by imposing a constraint (representing a limit on the radiation dose to be received by the healthy tissue) on specifically-identified healthy tissues and determining a treatment plan while observing that constraint.

Pursuant to another known approach, instead of using a same constraint value for all portions of the healthy tissue, the constraint can vary spatially such that healthy tissue closer to the targeted volume is imposed with a higher constraint value while healthy tissue further away from the treatment volume is imposed with a lower constraint value. Generally speaking this approach seeks to observe a rapid fall-off in dosing levels as the distance from the target volume increases and accordingly the fall-off curve is presumed/represented as being exponential.

While suitable for at least some application settings, the foregoing approaches do not necessarily meet all needs in these regards.

BRIEF DESCRIPTION OF THE DRAWINGS

The above needs are at least partially met through provision of the apparatus and method pertaining to determining a spatially-variant normal tissue constraint as a function of dose distribution described in the following detailed description, particularly when studied in conjunction with the drawings, wherein.

Figure 1:
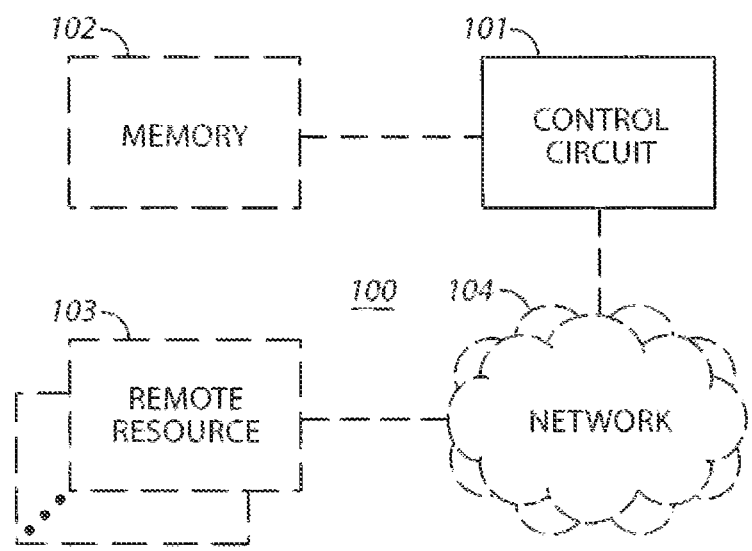
FIG. 1 comprises a block diagram as configured in accordance with various embodiments of the disclosed concept.

Elements in the figures are illustrated for simplicity and clarity and have not necessarily been drawn to scale. For example, the dimensions and/or relative positioning of some of the elements in the figures may be exaggerated relative to other elements to help to improve understanding of various embodiments of the present invention. Also, common but well-understood elements that are useful or necessary in a commercially feasible embodiment are often not depicted in order to facilitate a less obstructed view of these various embodiments of the present invention. Certain actions and/or steps may be described or depicted in a particular order of occurrence while those skilled in the art will understand that such specificity with respect to sequence is not actually required. The terms and expressions used herein have the ordinary technical meaning as is accorded to such terms and expressions by persons skilled in the technical field as set forth above except where different specific meanings have otherwise been set forth herein.

DETAILED DESCRIPTION

Generally speaking, pursuant to these various embodiments, a control circuit optimizes a radiation-treatment plan (as regards treating at least one target volume for a given patient) by, at least in part, automatically determining a spatially-variant normal tissue constraint as a function, at least in part, of dose distribution. By one approach this dose distribution constitutes dose distribution for other than the target volume itself (such as dose distribution for normal tissue that is proximal to the target volume). If desired, the control circuit can repeatedly determine spatially-variant normal tissue constraints while optimizing the radiation-treatment plan.

By one approach, this automatic determination comprises evaluating dose distributions at different distances from the target volume. So configured, the control circuit can effect such evaluation by penalizing, during the optimization of the radiation-treatment plan, dose distribution levels that exceed a predetermined distribution property (such as an aggregation value for the dose values including, but not limited to, an average value of dose values for each of the given specific different distances) at a given one of the specific different distances.

By permitting what effectively comprises a free-form function (as versus, for example, strict adherence to a presumed exponential function) to prevail with respect to dosing-level fall off (around and about a target volume) these teachings are well suited to leverage the strengths of an incremental optimization process and to achieve treatment results that are often better suited to accommodate the real-world presentation of a given patient. So configured, radiation-treatment plans that provide a desired level of dosing to a target volume while also tending to minimize undue collateral exposure to normal tissue (including critical organs) in the vicinity of the target volume are possible notwithstanding treatment circumstances that might otherwise frustrate such a result. These teachings are also highly flexible and scalable in practice and will readily accommodate a variety of specified or relevant distances, distance granularity, and radiation-exposure angles and energy levels.

These and other benefits may become clearer upon making a thorough review and study of the following detailed description. Referring now to the drawings, and in particular to FIG. 1, these teachings are presumably carried out by a corresponding apparatus 100 that includes a control circuit 101 of choice. Such a control circuit 101 can comprise a fixed-purpose hard-wired platform or can comprise a partially or wholly programmable platform. These architectural options are well known and understood in the art and require no further description here. This control circuit 101 is configured (for example, by using corresponding programming as will be well understood by those skilled in the art) to carry out one or more of the steps, actions, and/or functions described herein.

By one optional approach this control circuit 101 operably couples to a memory 102. This memory 102 may be integral to the control circuit 101 or can be physically discrete (in whole or in part) from the control circuit 101 as desired. This memory 102 can also be local with respect to the control circuit 101 (where, for example, both share a common circuit board, chassis, power supply, and/or housing) or can be partially or wholly remote with respect to the control circuit 101 (where, for example, the memory 102 is physically located in another facility, metropolitan area, or even country as compared to the control circuit 101).

By one approach, this memory 102 can serve, for example, to non-transitorily store the computer instructions that, when executed by the control circuit 101, cause the control circuit 101 to behave as described herein. (As used herein, this reference to "non-transitorily" will be understood to refer to a non-ephemeral state for the stored contents (and hence excludes when the stored contents merely constitute signals or waves) rather than volatility of the storage media itself and hence includes both non-volatile memory (such as read-only memory (ROM) as well as volatile memory (such as an erasable programmable read-only memory (EPROM).)

Also if desired, this control circuit 101 can operably couple to one or more remote resources 103 via one or more intervening networks 104 (such as but certainly not limited to the Internet). These remote resources 103 can serve to provide, for example, the dose distribution information described herein. In such a case this dose distribution information can be provided in a raw, unprocessed form or can be presented in a processed, ready-to-use form as desired. (This reference to "remote" will be understood to refer to a significant physical separation as when the remote resource 103 is physically located in another facility, metropolitan area, or even country as compared to the control circuit 101.)

The foregoing control circuit 101 is configured to optimize a radiation-treatment plan to treat at least one target volume (such as, but not limited to, a cancerous tumor) for a given patient. The present teachings will accommodate a wide variety of radiation-treatment machines and approaches including treatments that provide, during a single treatment session, for exposing the target volume to a radiation dose from each of a variety of different angles. These teachings will also accommodate radiation-treatment plans that presume to span a plurality of successive treatment sessions where the individual sessions are separated by hours, days, weeks, or even months. As the present teachings are not particularly sensitive to the selection of any particular approach to radiation treatment, further elaboration in these regards is not provided here for the sake of brevity.

These teachings also presume that the control circuit 101 is configured to optimize the radiation-treatment plan using an iterative optimization process. This means that the control circuit 101 will calculate a (typically large) number of candidate plans using a variety of modifiable operating parameters (such as gantry angle, energy level, and aperture and angle settings for one or more multi-leaf collimators). The results of each candidate plan can be compared (to one another and/or to one or more treatment objectives) to identify either a best plan or to at least inform the iteration process during subsequent parameter iterations. As iterative optimization processes are again generally well known in the art, further description regarding such processes is not provided here except where pertinent to the description. (It will also be understood that the present teachings are not limited to the use of an iterative optimization process and that such an application setting is only being presumed here for the sake of an illustrative example.)

Pursuant to these teachings the control circuit 101 optimizes the radiation-treatment plan by, at least in part, automatically determining a spatially-variant normal tissue constraint as a function, at least in part, of dose distribution. Generally speaking, as used herein, a constraint comprises a limit on the radiation dose to be received by healthy tissue as versus to be received by the target volume itself. Such a constraint serves as an objective for the control circuit 101 to employ when making automated iterative changes to operating parameters during the optimization process and when assessing the value and worth of a given candidate radiation-treatment plan. (Further information regarding such constraints can be found in U.S. patent application Ser. No. 11/698,617, entitled Spatially-Variant Normal Tissue Objective for Radiotherapy, the full contents of which are fully incorporated herein by this reference.)

Accordingly, a spatially-variant normal tissue constraint comprises a constraint regarding received radiation that varies with space (i.e., in this case, distance from the target volume).

The foregoing can comprise, at least in part, evaluating dose distributions at specific different distances from a target volume (such as the geometric center of the target volume or, perhaps more usefully, from a closest point on the periphery of the target volume) for a plurality of different patients. By one approach, such information can be culled from historical data in these regards.

Figure 2:
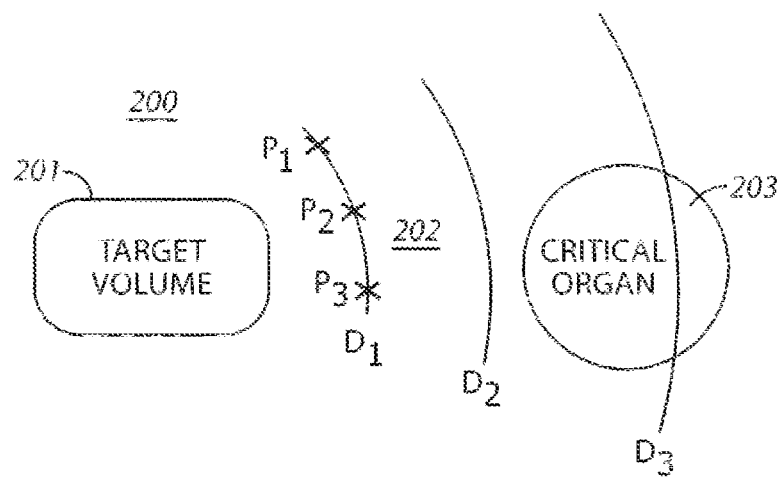
FIG. 2 comprises a schematic representation as configured in accordance with various embodiments of the disclosed concept.

FIG. 2 provides a highly-simplified example in these regards. FIG. 2 depicts at least a portion of a patient's body 200 that includes a target volume 201 that is surrounded by healthy tissue 202 (the latter including, in this example, a critical organ 203 as well). FIG. 2 also illustrates three lines D1-D3 that each illustrate a given corresponding distance from the target volume 201. The line denoted D1, for example, might represent a distance of 1 centimeter, while the line denoted D2 represents a distance of 2 centimeters and so forth.

For a variety of reasons it is not necessarily true that all points along any given equidistant line will receive an identical dose of radiation in a given treatment instance. Instead, there are likely to be variations in these regards. Accordingly, and by way of a simple example, the line corresponding to distance D1 has a first point P1 that receives 4.5 Gy of radiation, a second point P2 that receives 4.8 Gy of radiation, and a third point P3 that receives 4.9 Gy of radiation.

These teachings will accommodate calculating a distribution property for each such distance by calculating an aggregation value for some or all of the dose values as correspond to each such distance. As one simple example in these regards, the aggregation value can comprise an average value of the dose values for each of the specific different distances.

Using that approach, for example, a value of 4.7 Gy could be calculated as the distribution property for the distance D1.

If desired, such an aggregation value can be weighted as well. By one simple approach the aggregation value can be weighted by multiplying the aggregation result (such as the calculated average) by some predetermined constant. The value of the constant can of course vary with the application setting, specific optimization approach, and other influences and objectives that may be applicable.

These teachings will also accommodate calculating such dose distributions using information from a plurality of different patients. By one approach, all of the dose values for healthy tissue at a specific distance from the target volume for each of the plurality of different patients can be aggregated to provide a corresponding representative spatially-variant normal tissue radiation-dosing value for each of a plurality of different distances. These values, in turn, can be used to determine the aforementioned spatially-variant normal tissue constraints. For example, when the representative spatially-variant normal tissue radiation-dosing value for the distance D1 is, say, 4.7 Gy, then the spatially-variant normal tissue constraint for that same distance could be set to 4.7 Gy as well, or to some smaller or larger value as may be specified.

Using such an approach, the control circuit 101 can determine, for example, that a given candidate radiation-treatment plan that yields, at one point, a radiation dosing of 4.9 Gy for healthy tissue that is distance D1 from the target volume is likely unacceptably high. This determine rests upon a solid basis in fact that, on average, effective radiation-treatment plans manage to do better in those particular regards. Accordingly, the control circuit 101 can use this observation/conclusion to decide to continue optimizing and/or to select another candidate plan in lieu of the present plan.

As a more specific example in these regards, during the optimization process the control circuit 101 can penalize a dose distribution level that exceeds a predetermined distribution property at a given specific distance as described above. This penalization need not necessarily result in an abandonment of the offending plan but can provide one more way by which the overall efficacy of the plan can be accessed in an automated fashion. As a simple example in these regards, if candidate plans are rated (with respect to overall efficacy) using a 100 point scale (with a score of 100 representing a best possible plan), then a given value (such as 0.5, or 1.0, or some other appropriate number) can be subtracted from a present score for the plan for each point where the plan yields a radiation dosing of healthy tissue that exceeds the aforementioned spatially-variant constraint.

These teachings are highly flexible in practice and will accommodate a wide variety of variations. For example, by one approach, historical data regarding the dosing of healthy tissue can be mined as described to take special note of distances that happen to also coincide with a given critical organ (or critical organ tissue in general). Optimization planning often takes special care to avoid over-radiating critical organs and hence one may expect that spatially-variant dosing results over time will reflect this added caution. This approach, in turn, can permit the overall dosing of a given critical organ for the present patient to be calculated/estimated in a more accurate and less-generalized way. This more-accurate dosing result for the critical organ, in turn, can provide yet another useful metric by which one candidate plan can be compared to another to identify a best plan overall for a given patient.

As another example of the flexibility of these teachings, the control circuit 101 can be configured to automatically (or, if desired, via aided manual adjustment where a user makes step-wise changes with reach spatial dose distribution) determine spatially-variant normal tissue constraints by repeatedly determining spatially-variant normal tissue constraints during the optimization process. In other words, the resultant constraints themselves as informed by the aforementioned historical dosing distributions can themselves be treated in a dynamic manner as desired.

So configured, these teachings permit the control circuit 101 to make a considerably more nuanced and better informed automated analysis of plan efficacy for a given patient. In particular, the control circuit 101 can now assess whether a given plan seems better or worse than comparable historical results of a point-by-point basis through the healthy tissue that surrounds the target volume. So configured, useful planning results may be obtained in less time and/or better plans might be achieved than were otherwise achieved using prior approaches.

Those skilled in the art will recognize that a wide variety of modifications, alterations, and combinations can be made with respect to the above described embodiments without departing from the spirit and scope of the invention, and that such modifications, alterations, and combinations are to be viewed as being within the ambit of the inventive concept.

We claim:

1. An apparatus comprising:
a control circuit configured to optimize a radiation-treatment plan to treat at least one target volume for a given patient by, at least in part:
automatically determining a spatially-variant normal tissue constraint as a function, at least in part, of dose distribution.

2. The apparatus of claim 1 wherein the dose distribution constitutes dose distribution for other than the at least one target volume.

3. The apparatus of claim 2 wherein the dose distribution comprises dose distribution for normal tissue proximal to the at least one target volume.

4. The apparatus of claim 1 wherein the control circuit is configured to automatically determine the spatially-variant normal tissue constraint as a function, at least in part, of dose distribution by, at least in part, evaluating dose distributions at specific different distances from at least one target volume.

5. The apparatus of claim 4 wherein the control circuit is configured to evaluate the dose distributions at specific different distances from the at least one target volume by, at least in part, penalizing, during the optimization of the radiation-treatment plan, dose distribution levels that exceed a predetermined distribution property at a given one of the specific different distances.

6. The apparatus of claim 5 wherein the predetermined distribution property for a given one of the specific different distances comprises an aggregation value of dose values for a given one of the specific different distances.

7. The apparatus of claim 6 wherein the aggregation value comprises an average value of dose values for the given one of the specific different distances.

8. The apparatus of claim 7 wherein the aggregation value comprises the average value as weighted by a predetermined constant.

9. The apparatus of claim 1 wherein the control circuit is configured to automatically determine the spatially-variant normal tissue constraint by repeatedly determining spatially-variant normal tissue constraints while optimizing the radiation-treatment plan.

10. A method comprising:
by a control circuit configured to optimize a radiation-treatment plan to treat at least one target volume for a given patient:
automatically determining a spatially-variant normal tissue constraint as a function, at least in part, of dose distribution.

11. The method of claim 10 wherein the dose distribution constitutes dose distribution for other than the at least one target volume.

12. The method of claim 11 wherein the dose distribution comprises dose distribution for normal tissue proximal to the at least one target volume.

13. The method of claim 10 wherein automatically determining the spatially-variant normal tissue constraint as a function, at least in part, of dose distribution comprises, at least in part, evaluating dose distributions at specific different distances from at least one target volume.

14. The method of claim 13 wherein evaluating the dose distributions at specific different distances from the at least one target volume comprises, at least in part, penalizing, during the optimization of the radiation-treatment plan, dose distribution levels that exceed a predetermined distribution property at a given one of the specific different distances.

15. The method of claim 14 wherein the predetermined distribution property for a given one of the specific different distances comprises an aggregation value of dose values for a given one of the specific different distances.

16. The method of claim 15 wherein the aggregation value comprises an average value of dose values for the given one of the specific different distances.

17. The method of claim 16 wherein the aggregation value comprises the average value as weighted by a predetermined constant.

18. The method of claim 10 wherein automatically determining the spatially-variant normal tissue constraint comprises repeatedly determining spatially-variant normal tissue constraints while optimizing the radiation-treatment plan.

* * * * *